(12) United States Patent
Theodore et al.

(10) Patent No.: US 11,096,721 B2
(45) Date of Patent: Aug. 24, 2021

(54) POST-OPERATIVE PREDICTION

(71) Applicant: 360 Knee Systems Pty Ltd, New South Wales (AU)

(72) Inventors: Willy Theodore, New South Wales (AU); Joshua Twiggs, New South Wales (AU); Brad Miles, New South Wales (AU); Bede O'Connor, New South Wales (AU)

(73) Assignee: 360 Knee Systems Pty Ltd., New South Wales (AU)

( * ) Notice: Subject to any disclaimer, the term of this patent is extended or adjusted under 35 U.S.C. 154(b) by 245 days.

(21) Appl. No.: 15/747,317

(22) PCT Filed: Jul. 25, 2016

(86) PCT No.: PCT/AU2016/050661
§ 371 (c)(1),
(2) Date: Jan. 24, 2018

(87) PCT Pub. No.: WO2017/020069
PCT Pub. Date: Feb. 9, 2017

(65) Prior Publication Data
US 2018/0214180 A1 Aug. 2, 2018

(30) Foreign Application Priority Data
Jul. 31, 2015 (AU) .................................. 2015903060

(51) Int. Cl.
*A61B 17/56* (2006.01)
*A61B 34/10* (2016.01)
(Continued)

(52) U.S. Cl.
CPC .............. *A61B 17/56* (2013.01); *A61B 5/055* (2013.01); *A61B 6/032* (2013.01); *A61B 6/505* (2013.01);
(Continued)

(58) Field of Classification Search
CPC ... A61B 17/56; A61B 34/10; A61B 2034/105; A61B 2034/108
See application file for complete search history.

(56) References Cited

U.S. PATENT DOCUMENTS

| 6,161,080 | A  | 12/2000 | Aouni-Ateshian et al. |
| 2003/0153978 | A1 | 8/2003 | Whiteside et al. |

(Continued)

FOREIGN PATENT DOCUMENTS

| WO | 2003/041566 A2 | 5/2003 |
| WO | 2006/078236 A1 | 7/2006 |

OTHER PUBLICATIONS

An Interactive Graphics-Based Model of the Lower Extremity to Study Orthopaedic Surgical Procedures by Scott et al. published in IEEE Transactions on Biomedical Engineering. vol. 37. No. 8. Aug. 1990 (Year: 1990).*

(Continued)

*Primary Examiner* — Gary Jackson
*Assistant Examiner* — Zahed Kabir
(74) *Attorney, Agent, or Firm* — Kilpatrick Townsend & Stockton LLP

(57) ABSTRACT

This disclosure relates to methods and systems to assist in surgery of a joint. The system determines a mechanical property of one or more ligaments associated with the joint based on measurement data indicative of a movement of the bones relative to each other under multiple mechanical loads. The system then determines a predicted characteristic of the joint after the surgery based on a spatial parameter of the surgery and based on the mechanical property of the one or more ligaments and generates an output signal indicative of the predicted characteristic to assist the surgery. Since the predicted characteristic of the joint is determined based on the mechanical property of the ligaments, the prediction is (Continued)

more accurate than other methods that rely on only bone geometries to predict a surgery outcome.

21 Claims, 12 Drawing Sheets

(51) Int. Cl.
    *A61B 6/00*         (2006.01)
    *G16H 50/30*       (2018.01)
    *A61B 5/055*       (2006.01)
    *A61B 6/03*         (2006.01)
    *A61F 2/46*         (2006.01)
    *G16H 50/50*       (2018.01)

(52) U.S. Cl.
    CPC ............ *A61B 6/5217* (2013.01); *A61B 34/10* (2016.02); *A61F 2/46* (2013.01); *G16H 50/30* (2018.01); *G16H 50/50* (2018.01); *A61B 2034/104* (2016.02); *A61B 2034/105* (2016.02)

(56) References Cited

U.S. PATENT DOCUMENTS

| | | | |
|---|---|---|---|
| 2005/0119661 A1* | 6/2005 | Hodgson | A61B 17/155 606/90 |
| 2009/0132217 A1* | 5/2009 | Nakamura | G09B 23/32 703/2 |
| 2010/0076563 A1 | 3/2010 | Otto et al. | |
| 2013/0110250 A1 | 5/2013 | Li et al. | |
| 2014/0019110 A1* | 1/2014 | Otto | A61B 5/103 703/11 |
| 2014/0244220 A1* | 8/2014 | McKinnon | A61B 34/10 703/1 |
| 2015/0193590 A1* | 7/2015 | Miles | G16H 50/50 700/98 |
| 2016/0045317 A1* | 2/2016 | Lang | A61F 2/30942 700/98 |

OTHER PUBLICATIONS

"International Search Report" issued in PCT/AU2016/050661, dated Oct. 13, 2016, 5 pages.

International Preliminary Report on Patentability issued in in PCT/AU2016/050661, dated Jul. 25, 2017, 9 pages.

Blankevoort et al., Articular Contact in a Three-Dimensional Model of the Knee, Journal of Biomechanics, vol. 24, No. 11, Available online at: https://core.ac.uk/download/pdf/11476415.pdf, Jan. 1, 1991, pp. 1019-1031.

European Patent Application No. 16831963.0, Extended European Search Report dated Feb. 25, 2019, 9 pages.

Martelli et al., Total Knee Arthroplasty Kinematics, Computer Simulation and Intraoperative Evaluation, The Journal of Arthroplasty vol. 13, No. 2, 1998, pp. 145-155.

* cited by examiner

3° varus

0°

3° valgus

4° varus

1° varus

2° valgus

POST-OPERATIVE PREDICTION

CROSS-REFERENCE TO RELATED APPLICATIONS

The present application is a U.S. National Stage of International Application No. PCT/AU2016/050661 filed on Jul. 25, 2016, which claims priority from Australian Provisional Patent Application No 2015903060 filed on 31 Jul. 2015. Each of these applications is hereby incorporated by reference in its entirety for all purposes.

TECHNICAL FIELD

This disclosure relates to methods and systems to assist in surgery of a joint.

BACKGROUND

The success of orthopedic surgery often depends on a spatial parameter of the surgery, such as the angle at which a bone is cut in order to attach an implant, such as an artificial joint. For example, the cutting angle of the tibia for a knee replacement influences the degree of varus/valgus, which is also known as bow-legged/cross-legged.

In many cases, surgeons have the experience and knowledge to decide on a cutting angle or use computers to calculate an optimal cutting angle. However, in many cases the actual outcome of the surgery is not optimal, that is, the patient is less mobile after the surgery than what would be possible with a different cutting angle.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

There is disclosed a method for assisting surgery of a joint comprising a kinematic system of two bones. The method comprises:

determining a mechanical property of one or more ligaments associated with the joint based on measurement data indicative of a movement of the bones relative to each other under multiple mechanical loads;

determining a predicted characteristic of the joint after the surgery based on a spatial parameter of the surgery and based on the mechanical property of the one or more ligaments; and generating an output signal indicative of the predicted characteristic to assist the surgery.

Since the predicted characteristic of the joint is determined based on the mechanical property of the ligaments, the prediction is more accurate than other methods that rely on only bone geometries to predict a surgery outcome. This is an advantage because the surgeon can plan the surgery more accurately, which also means the patient outcome will be improved. As a result, treated patients have increased quality of live as they are able to perform more activities due to the improved surgery outcome.

The kinematic system may comprise three or more bones.

The three or more bones may comprise tibia, patella and femur.

The spatial parameter of the surgery may be a cutting angle for attaching an implant.

Determining the predicted characteristic may comprise determining a predicted laxity of the joint.

Generating the output signal may comprise generating a display of the predicted characteristic.

The method may further comprise using the output signal to optimise the spatial parameter of the surgery.

Optimising the spatial parameter of the surgery may comprise adjusting a pre-defined value of the spatial parameter of the surgery.

The method may further comprise determining the measurement data based on multiple first images, each of the multiple first images representing a position of the bones relative to each other under the respective mechanical load.

Each of the multiple first images may be an X-ray image of the joint.

The method may further comprise determining the measurement data based on contact-based data representing a position of the bones relative to each other under the respective mechanical load.

Determining the mechanical property may comprise determining the mechanical property based on a spatial configuration of the joint.

The method may further comprise determining the spatial configuration of the joint based on a second image of the joint.

Determining the spatial configuration of the joint may comprise determining the spatial configuration of the joint based on a 3D scan of the joint.

Determining the spatial configuration of the joint may comprise determining the spatial configuration of the joint based on a CT scan or MRI scan or both.

Determining a mechanical property may comprise determining a stiffness value or a length value or both of the one or more ligaments.

The length value may be indicative of a free-length, reference length or taut length.

The method may further comprise receiving input data indicative of a desired characteristic of the joint, wherein generating an output signal may comprise generating an output signal that is indicative of a correspondence between the desired characteristic and the predicted characteristic.

The method may further comprise determining a modification of the one or more ligaments to adjust the predicted characteristic towards the desired characteristic based on the spatial parameter of the surgery and based on the mechanical property of the one or more ligaments, wherein generating an output signal comprises generating an output signal that is indicative of the modification of the one or more ligaments.

Determining the mechanical property of the one or more ligaments may comprise determining the mechanical property of the one or more ligaments based on measurement data indicative of the movement of the bones relative to each other under multiple angles between the two bones.

The joint may be a knee.

Software, when installed on a computer, causes the computer to perform the method of any one of the preceding claims.

There is disclosed a computer system for assisting surgery of a joint comprising a kinematic system of two bones. The computer system comprises:

an input port to receive measurement data indicative of a movement of the bones relative to each other under multiple mechanical loads;

a processor to determine a mechanical property of one or more ligaments associated with the joint based on the measurement data, and to determine a predicted characteristic of the joint after the surgery based on a spatial parameter of the surgery and based on the mechanical property of the one or more ligaments; and an output port for an output signal indicative of the predicted characteristic to assist the surgery.

Optional features described of any aspect of method, computer readable medium or computer system, where appropriate, similarly apply to the other aspects also described here.

BRIEF DESCRIPTION OF DRAWINGS

An example will be described with reference to.

DESCRIPTION OF EMBODIMENTS

Figure 1:
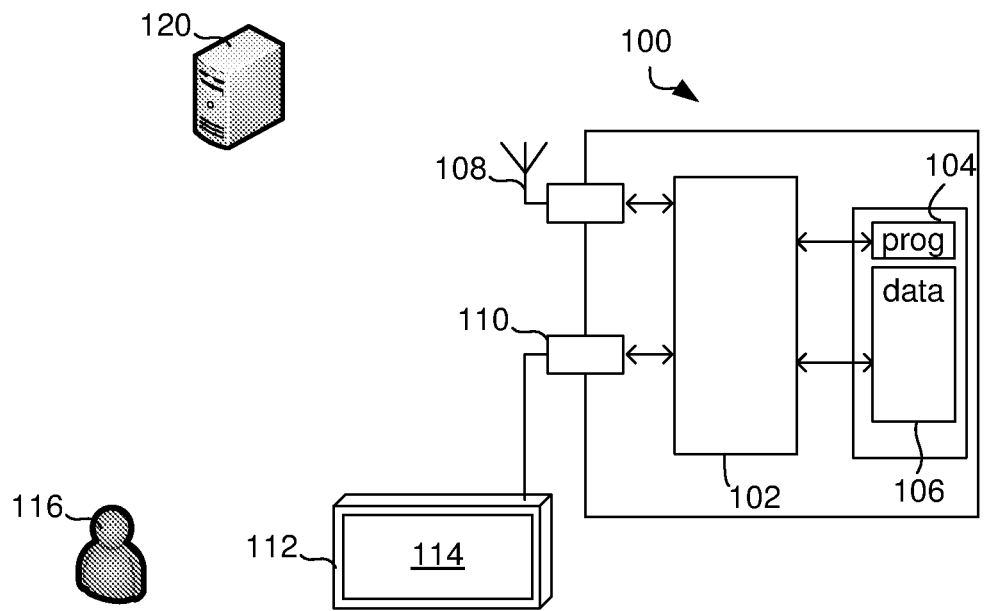
FIG. 1 illustrates a computer system for assisting surgery of a joint.

FIG. 1 illustrates a computer system 100 for assisting surgery of a joint. The computer system 100 comprises a processor 102 connected to a program memory 104, a data memory 106, a communication port 108 and a user port 110. The program memory 104 is a non-transitory computer readable medium, such as a hard drive, a solid state disk or CD-ROM. Software, that is, an executable program stored on program memory 104 causes the processor 102 to perform the method in FIG. 2, that is, processor 102 determines a mechanical property of the ligaments and a predicted post-operative characteristic, such as laxity of the joint. Laxity may be defined by a set of angles and/or movement of the joint under different loads and poses. The term "determining a laxity" refers to calculating one or more values that are indicative of the laxity.

The processor 102 may then store the laxity on data store 106, such as on RAM or a processor register. Processor 102 may also send the determined laxity via communication port 108 to a server, such as patient management database.

The processor 102 may receive data, such as X-ray image data, from data memory 106 as well as from the communications port 108 and the user port 110, which is connected to a display 112 that shows a visual representation 114 of the image data to a surgeon 116 or other user or operator. In one example, processor 102 receives image data from an X-ray, magnetic resonance imaging (MRI) or computer tomography (CT) imaging device via communications port 108, such as by using a Wi-Fi network according to IEEE 802.11. The Wi-Fi network may be a decentralised ad-hoc network, such that no dedicated management infrastructure, such as a router, is required or a centralised network with a router or access point managing the network.

Although communications port 108 and user port 110 are shown as distinct entities, it is to be understood that any kind of data port may be used to receive data, such as a network connection, a memory interface, a pin of the chip package of processor 102, or logical ports, such as IP sockets or parameters of functions stored on program memory 104 and executed by processor 102. These parameters may be stored on data memory 106 and may be handled by-value or by-reference, that is, as a pointer, in the source code.

The processor 102 may receive data through all these interfaces, which includes memory access of volatile memory, such as cache or RAM, or non-volatile memory, such as an optical disk drive, hard disk drive, storage server or cloud storage. The computer system 100 may further be implemented within a cloud computing environment, such as a managed group of interconnected servers hosting a dynamic number of virtual machines.

It is to be understood that any receiving step may be preceded by the processor 102 determining or computing the data that is later received. For example, the processor 102 determines measurement data and stores the measurement data in data memory 106, such as RAM or a processor register. The processor 102 then requests the data from the data memory 106, such as by providing a read signal together with a memory address. The data memory 106 provides the data as a voltage signal on a physical bit line and the processor 102 receives the measurement data via a memory interface.

It is to be understood that throughout this disclosure unless stated otherwise, nodes, edges, graphs, solutions, variables, surgery plans, dimensions, locations and the like refer to data structures, which are physically stored on data memory 106 or processed by processor 102. Further, for the sake of brevity when reference is made to particular variable names, such as "predicted characteristic" or "spatial parameter of the surgery" this is to be understood to refer to values of variables stored as physical data in computer system 100.

Figure 2:
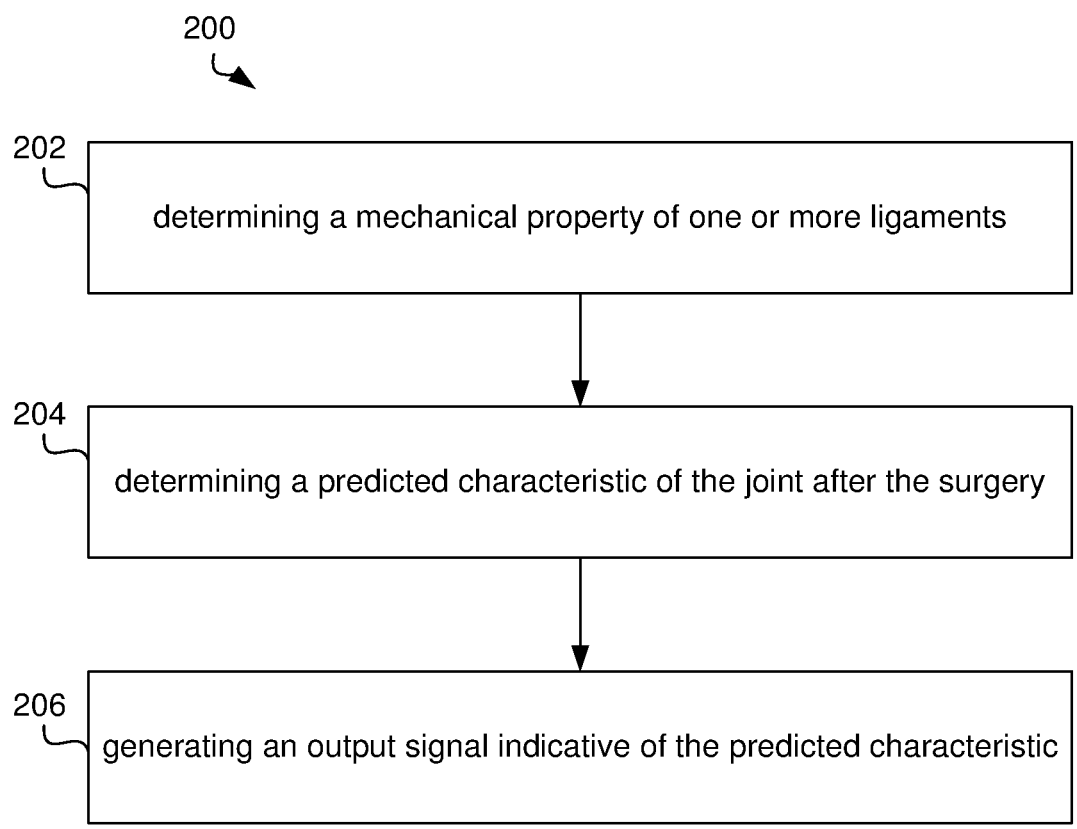
FIG. 2 illustrates a method for assisting surgery of a joint.

FIG. 2 illustrates a method 200 as performed by processor 102 for assisting surgery of a joint. FIG. 2 is to be understood as a blueprint for the software program and may be implemented step-by-step, such that each step in FIG. 2 is represented by a function in a programming language, such as C++ or Java. The resulting source code is then compiled and stored as computer executable instructions on program memory 104.

The joint comprises a kinematic system of two bones, such as the tibia and femur in the example of knee surgery or hip and femur in the example of hip surgery. The kinematic system may comprise more than two bones including the patella, for example.

Processor 102 commences performing method 200 by determining a mechanical property of one or more ligaments associated with the joint. For example, processor determines a stiffness and a length value, which may be a free length, a reference length or a taut length. This calculation is based on measurement data indicative of a movement of the bones relative to each other under multiple mechanical loads. In one example, processor 102 determines the measurement data based on multiple X-ray images, which are also referred to as 'first' images, and an MRI image, that is also referred to as 'second' image.

It is to be understood that 'image' may refer to a two-dimensional image, such in X-ray image stored on data memory 106 in the form of a two-dimensional pixel matrix comprising one intensity value for each pixel in the case of a grey scale image. However, 'image' may also refer to a three-dimensional image comprising multiple two-dimensional images, such as an MRI or CT image which a surgeon can peruse on a two-dimensional screen by selecting different depth values and different viewing angles. Two-dimensional and three-dimensional images may be stored on data memory 106 as multiple image values, such as in a two-dimensional or three-dimensional pixel matrix. In other examples, the images are stored in a parameterised representation, such as a spline representation and processor 102 generates a two-dimensional view on a screen by interpolation based on the spline parameters.

Figure 3A:
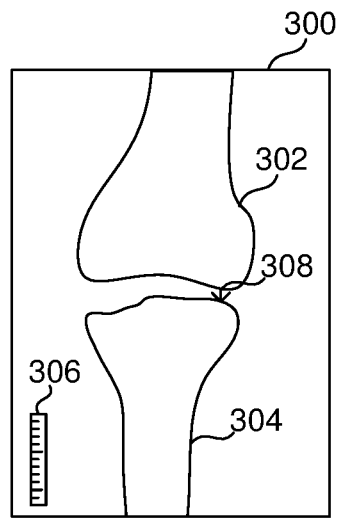
FIG. 3a illustrates an X-ray image of a knee joint in an unloaded state.

FIG. 3*a* illustrates an X-ray image 300 of a knee joint in an unloaded state, that is, the patient is lying without externally applied forces. X-ray image 300 shows the femur 302 the tibia 304 and an absolute reference 306 that was place next to the knee when taking the X-ray image. Processor 102 detects the edges of the femur 302 and tibia 304 using a Sobel operator, for example. In another example, processor 102 performs a method for 2D-3D image registration as described in the following publications, which are incorporated herein by reference:

Youngjun Kim, Kang-Il Kim, Jin hyeok Choi, Kunwoo Lee, "Novel methods for 3D postoperative analysis of total knee arthroplasty using 2D-3D image registration", Clinical Biomechanics 26 (2011) 384-391;

Guoyan Zheng, Xuan Zhang "Computer assisted determination of acetabular cup orientation using 2D-3D image registration", International Journal of Computer Assisted Radiology and Surgery, September 2010, Volume 5, Issue 5, pp 437-447; and Guoyan Zheng, Simon Steppacher, Xuan Zhang, Moritz Tannast, "Precise Estimation of Postoperative Cup Alignment from Single Standard X-Ray Radiograph with Gonadal Shielding", Medical Image Computing and Computer-Assisted Intervention—MICCAI 2007, Lecture Notes in Computer Science Volume 4792, 2007, pp 951-959.

Processor 102 then determines a minimum distance 308 between the femur 302 and tibia 304 as a number of image pixels. Processor 102 can then detect the absolute scale 306 to transform the number of image pixels into an absolute measurement in millimetres, for example.

Figure 3B:
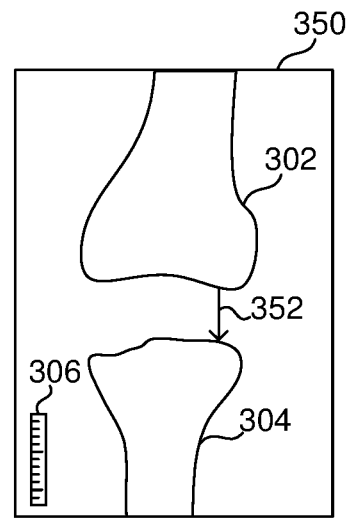
FIG. 3b illustrates an X-ray image of the knee joint in a loaded state.

FIG. 3*b* illustrates an X-ray image 350 of the knee joint in a loaded state. In this example, the patient is standing on one leg on a step and a weight is attached to the foot of the other leg that is relaxed and hangs off the step. As can be seen in FIG. 3*b* there has been movement of the femur 302 and the tibia 304 relative to each other under the two different mechanical loads, that is, a movement between FIG. 3*a* and FIG. 3*b*. Again processor 102 detects the edges of femur 302 and tibia 304 and determines a minimum distance 352 in millimetres between them. Processor 102 can then calculate the change in distance from 308 to 352 as well as rotation difference, which is indicative of the relative movement of the femur 302 in relation to the tibia 304 or vice versa.

Since the distance 352 under load depends on the mechanical characteristics of the ligaments, processor 102 can determine these mechanical characteristics based on a mechanical model and the measured distances 308 and 352.

Figure 4A:
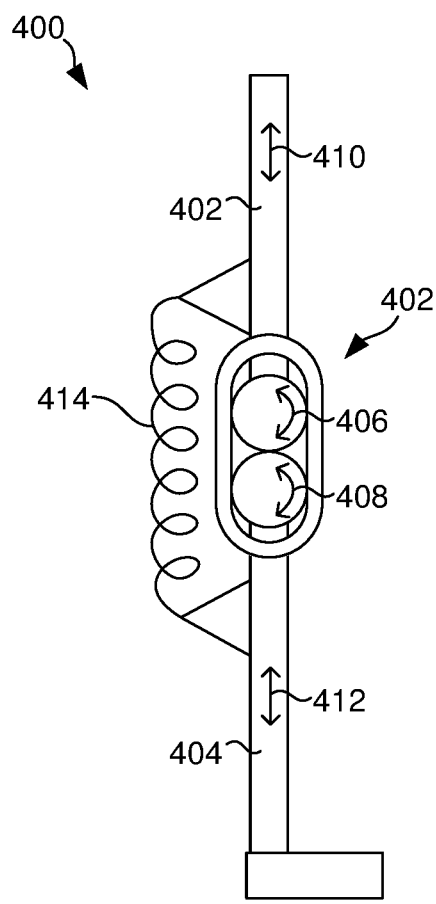
FIG. 4a illustrates a simplified mechanical model of the knee in the unloaded state.
Figure 4B:
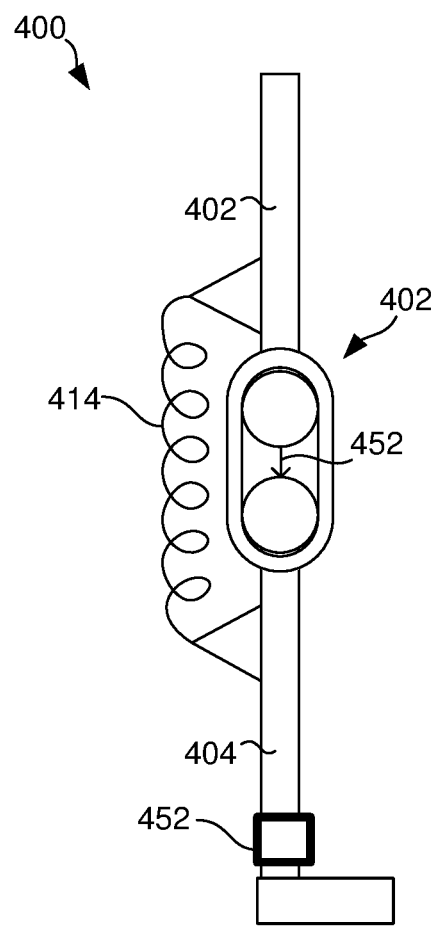
FIG. 4b illustrates the mechanical model of the knee in the loaded state.

FIG. 4*a* illustrates a simplified mechanical model 400 of the knee in the unloaded state related to X-ray image 300 while FIG. 4*b* illustrates the mechanical model of the knee in a loaded state related to X-ray image 350. In this example, the mechanical model 400 comprises an upper rod 402 representing the femur 302 and a lower rod 404 representing the tibia 304. The two rods 402 and 404 are mechanically coupled by a joint 402 that allows rotation with one degree of rotational freedom as indicated by arrows 406 and 408 to model the flexion and extension of a human knee. Joint 402 also allows translational movement with one degree of freedom as indicated by arrows 410 and 412 to represent stretching of the knee under load. The translational movement 410 and 412 is restricted by a spring 414, that is, spring 414 pulls the upper rod 402 towards the lower rod 404 with a force that increases with the distance between the upper rod 402 and the lower rod 404.

FIG. 4*b* illustrates the mechanical model 400 of the knee as in FIG. 4*a* but now the mechanical model is under load as shown in X-ray image of FIG. 3*b*. FIG. 4*b* illustrates a weight 452 that is attached to the lower rod 404. As a result of the weight 452 there is translational movement of the lower rod 404 in relation to the upper rod 402 against the pull force of spring 414 resulting in a distance 452 in the joint 402. In this example, it is assumed that the distance in the joint is zero in the unloaded case in FIG. 4*a* for simplicity.

The force F applied by spring 414 with spring constant k at length x is F=−kx, which can be re-arranged to $$k = \frac{-F}{x}.$$

is the force applied by weight 452, such as 5 kg, and x is the measured movement 452, both of which are stored on data memory 106. As a result, processor 102 can determine the spring constant k, which is also referred to as the stiffness value of the ligament. By setting the value for F to zero, processor 102 can also calculate the free length, which is the result for x given the determined spring constant k and F=0.

While the example of FIGS. 4*a* and 4*b* relates to determining the stiffness of only a single ligament, in other examples processor 102 determines the stiffness of multiple ligaments. For example, the knee can be separated into three physiological anatomical compartments: the patellofemoral compartment, the medial compartment, and the lateral compartment. The lateral compartment is bounded medially by the anterior cruciate ligament, laterally by the lateral capsular ligament, the ilio-tibial tract, and the fibula lateral ligament and posteriorly by the arcuate complex and the posterior capsule. These structures are all supported by the iliotibial band, the poplitius muscle, the biceps muscle and an extension of the semimembranosus muscle called the oblique popliteal ligament.

The medial compartment is bounded medially by the deep third of the mid-capsular ligament, the medial collateral ligament, and the posterior oblique ligament and laterally by the posterior cruciate ligament. Anteriorly, these compartments have extensions of the medial capsule as well as patellotibial and patellofemoral expansions, as well as the patella tendon.

Since each ligament may have a different stiffness value and free-length value, processor 102 may determine the movement 352 for multiple different mechanical loads. Each ligament generates another unknown in a linear system of equations based on the above formula and each measurement of a different load generates an observation. Preferably, the number of different loads is at least the number of ligaments. Further, the accuracy can be increased by having each linear equation linearly independent from the other equations. Therefore, the load may be applied to the knee at different flexion angels of the knee such that different ligaments are stretched at different angles.

The measurement data may comprise data generated by a stress device that applies the different mechanical loads to the knee. In one example, the stress device is a Telos stress device by Austin & Associates, Inc./Telos GmbH. It is noted that other devices may also be used to generate the measurement data.

Before processing the X-ray images of the loaded knee, processor 102 may determine the attachment locations of each ligament to the bone and the shape and size of the bones to refine the mechanical model 400. For example, the processor 102 may process an MRI scan of the bone. The ligaments are clearly visible on MRI but hardly visible on an X-ray image. However, it is difficult to apply mechanical force to the knee while taking an MRI scan due to the relatively long time the MRI scan takes and due to the strong magnetic field of the MRI scanner. Therefore, the MRI is only captured once to define the static characteristic of the joint, including the 3D geometries and landmarks from which to measure the movement, such as medial and lateral condyles. Then, multiple X-rays are captured at different loads and flexion angles.

Instead of the single distance measurement 352 of FIG. 3b, the measurement data may include multiple measurements for each mechanical load, such as distances from medial and lateral condyles to the tibia to define vargus and valgus. Processor 102 may further calculate a pre-operative characteristic of the knee, such as pre-op laxity.

Returning back to FIG. 2, after the mechanical properties of the ligaments are determined, processor determines 204 a predicted characteristic of the joint after the surgery, such as predicted post-op laxity. This step is based on a spatial parameter of the surgery and based on the previously determined mechanical property of the one or more ligaments. The surgery may comprise the insertion of an implant, which likely affects the three-dimensional geometries of the joint. In particular, the cut angle of the tibia on which the implant is mounted is an important spatial parameter that affects the angles of the knee. Other spatial parameters relate to the geometry of the particular implant. This geometry may be retrieved from an implant library that stores the geometries of a wide range of available implants. Processor 102 receives the data indicative of the planned cut angle and the geometries of the implant. Based on this data and the mechanical characteristic of the ligaments, processor 102 calculates a predicted characteristic of the knee after the surgery. That is, processor 102 applies the same loads as above on the mechanical model considering the determined ligament properties but now for a changed geometry as a result of the planned surgery. For example, processor 102 determines the post-operative varus/valgus values and post-operative laxity of the knee joint using spring constants k and new geometries.

Processor 102 then generates 206 an output signal indicative of the predicted characteristic to assist the surgery. In one example, the output signal is a display to be shown to the surgeon on a computer screen. The display may comprise numbers representing the determined varus/valgus at different stress test or may comprises a graphical indication of predicted post-operative laxity, such as curves of varus/valgus at applied moments to the model at different flexion angles. This informs the surgeon on whether the planned parameters of the operation are satisfactory or whether the cut angle for the implant should be adjusted, for example.

For example, the surgeon may perform a surgical technique called gap balancing where the surgeon cuts the tibia surface first then distracts the joint to find balance. Then the femoral component alignment, particularly rotation, is planned accordingly to achieve that balance. However, the definition of balance may differ between surgeons and may be subjective. By measuring the applied force or pressure during the joint distraction, processor 102 can generate an output signal that objectively indicates to the surgeon how to balance the knee based on the mechanical simulation model.

In another example, the output signal to assist the surgery is a feedback signal to a planning software that automatically optimises the spatial parameters, such as iteratively adjusts the cut angle until the output signal is indicative of a desired laxity. In that example, the surgeon may enter an intended cut angle which is received by the processor 102 as a pre-defined value of the spatial parameter of the surgery. If the output signal generated by processor 120 is indicative of an unsatisfactory laxity, the planning software adjusts the pre-define value to optimise the laxity.

In yet another example, the surgeon enters a desired laxity or the planning software determines a desired laxity based on particular activities that the patient wants to perform after the surgery. For example, kneeling down would be easier with a less tight knee, that is, more laxity, while playing tennis would be easier with a tighter knee, that is, less laxity. The output signal is then indicative of whether the predicted characteristic corresponds to the desired characteristic, such as by highlighting in red colour the values for relative movement or angles when processor 102 applies forces to the mechanical model as described above. The output signal may also be a data signal representing a report of the predicted characteristic of the joint after surgery. The report may also include the pre-operative characteristic.

Figure 5:
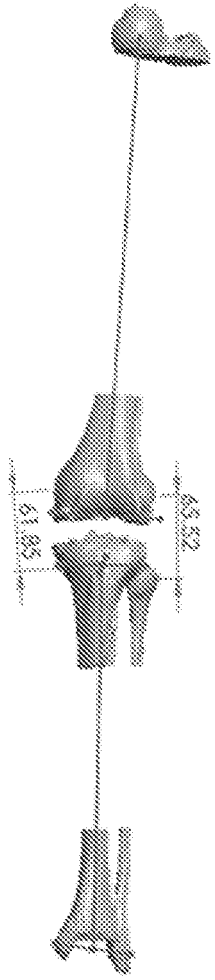
FIG. 5 illustrates a mechanical model of a knee under three different mechanical loads.
Figure 6:
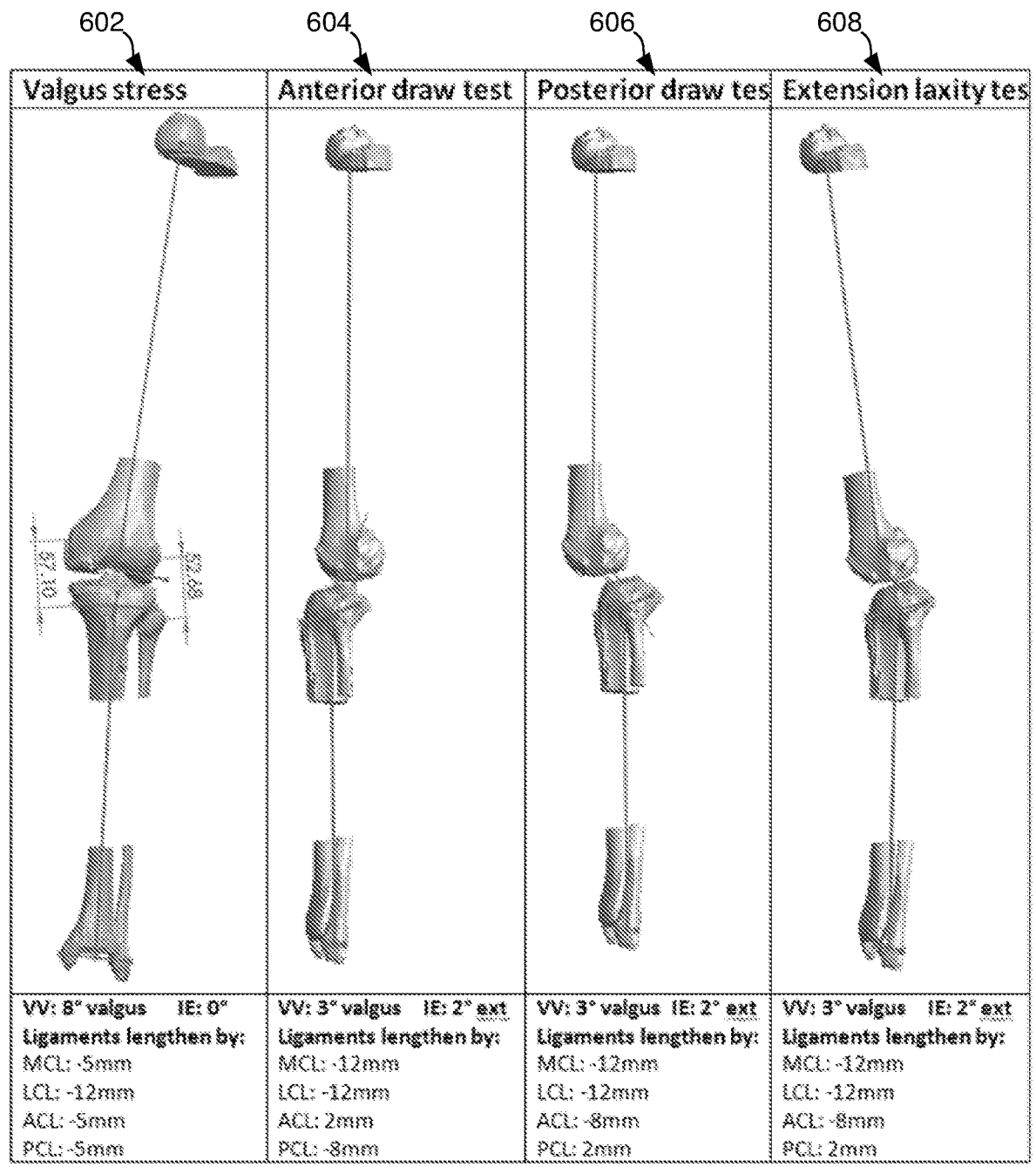
FIG. 6 illustrates the mechanical model of the knee under four further different mechanical loads.

FIG. 5 illustrates a mechanical model of a knee under three different mechanical loads, that is, while one leg is hanging 502, when the knee is weight bearing 504 and under varus stress 506. FIG. 6 illustrates the mechanical model of the knee under four further different mechanical loads, that is, valgus stress 602, anterior draw test 604, posterior draw test 606 and extension laxity test 608.

Figure 7A:
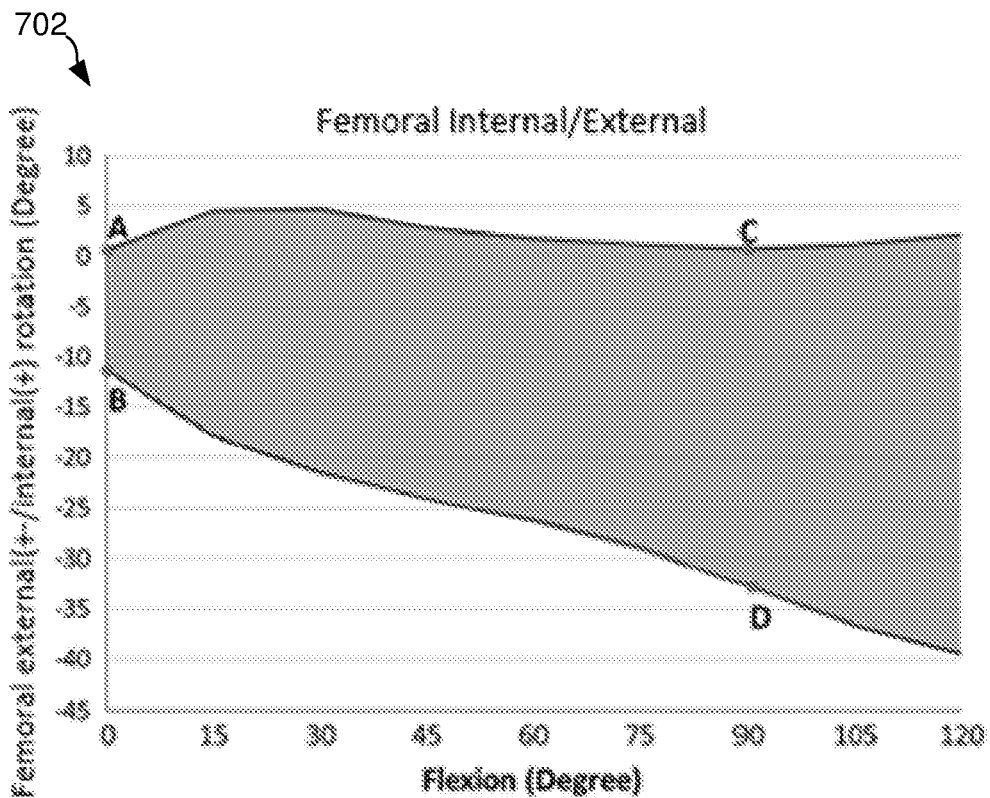
FIGS. 7a, 7b and 7c illustrate respective laxity envelopes.
Figure 7B:
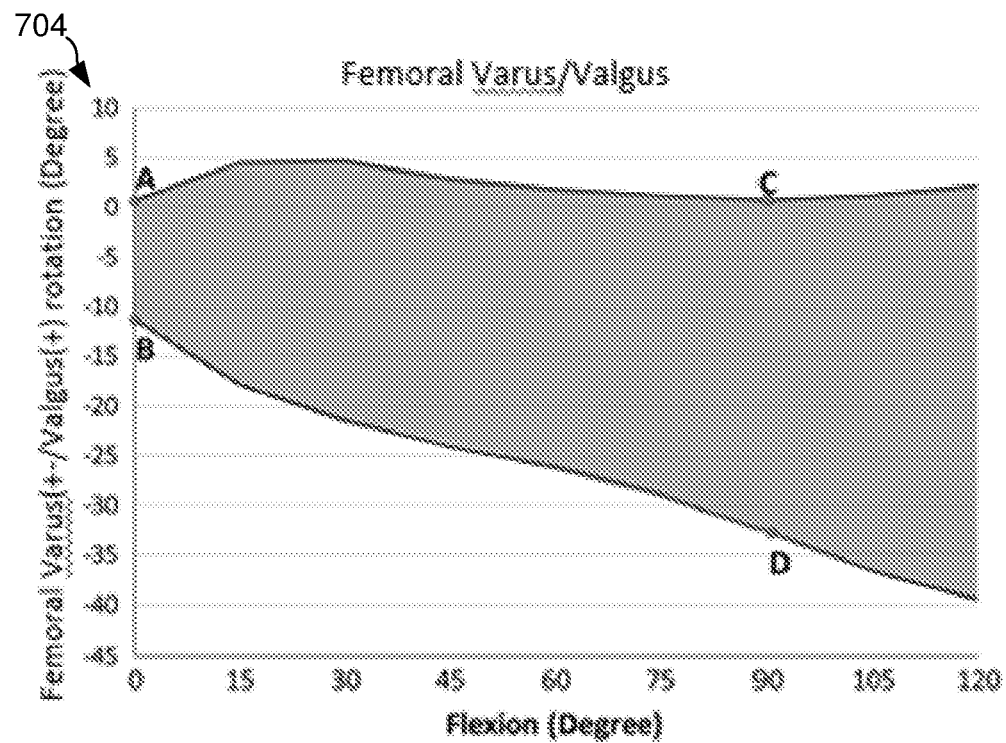
Figure 7C:
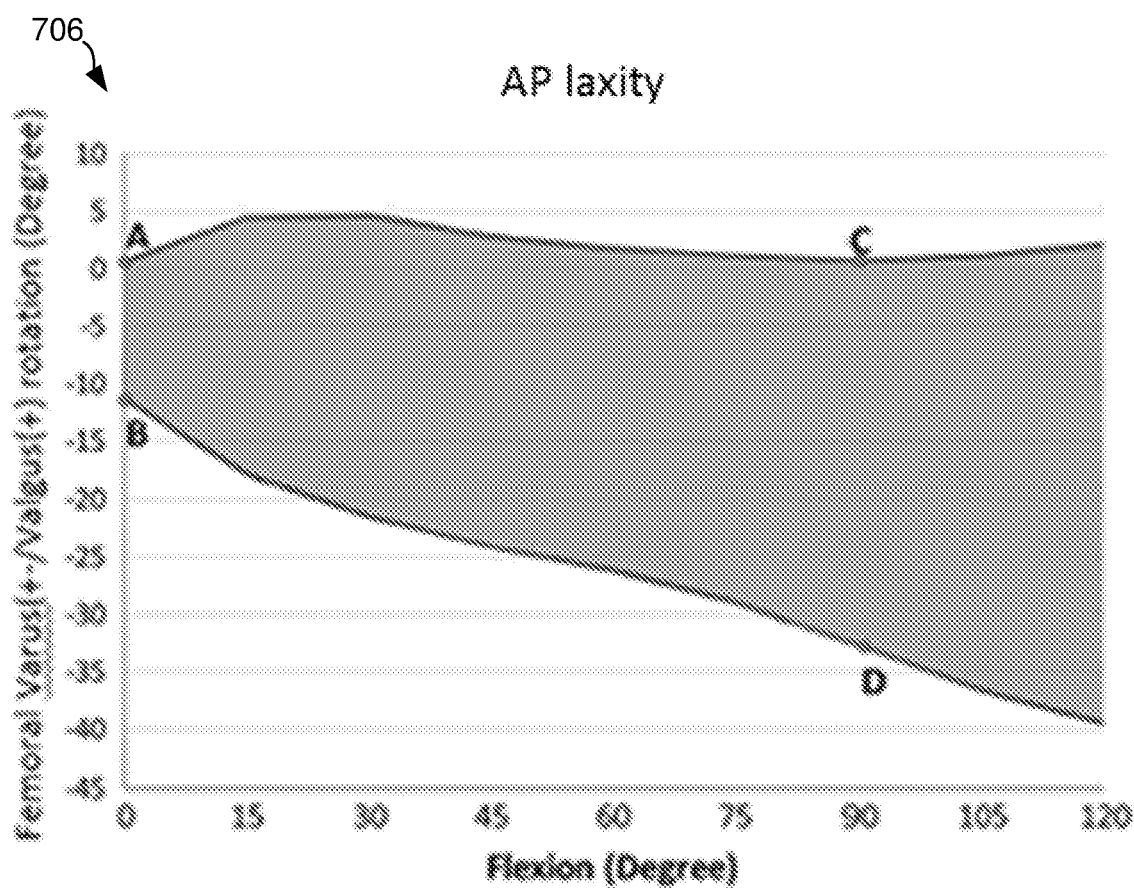

FIGS. 7a, 7b and 7c illustrate laxity envelopes for femoral internal/external rotation 702, femoral varus/valgus 704 and anterior/posterior laxity 706, respectively, over a range of flexion from 0 to 120 degrees.

In one example, the ligament laxity order is:

| Ligaments | Tight by percentage |
|---|---|
| LCL | 20% |
| MCL | 10% |
| PCL | — |

Implant System Details may be
Femoral Component: Omni Apex Right CR Femur Size 5
Tibial Component: Omni Apex Tibial Tray Size 6
Tibial Insert: Omni Apex CR Insert Size 5 10 mm
Patella Button: Omni Apex Patella Button Size 35 8 mm
Component Placement Information may be:

| | Femoral Component | Tibial Component | TibioFemoral Alignment |
|---|---|---|---|
| Sagittal: | 4.0° Flexion | 3.0° Slope | |
| Coronal: | 0.0° Varus | 0.0° Varus | 0.0° Varus |
| Transverse: | 0.0° Internal | 0.0° Internal | 0.0° Internal |
| AP position | 2 mm anterior from PCA | Best fit to resected tibia geometry | |
| SI position | Level with distal condyle | 11 mm cut from medial plateau | |
| ML position | Best fit to resected geometry | Best fit to resected geometry | |

Figure 8A:
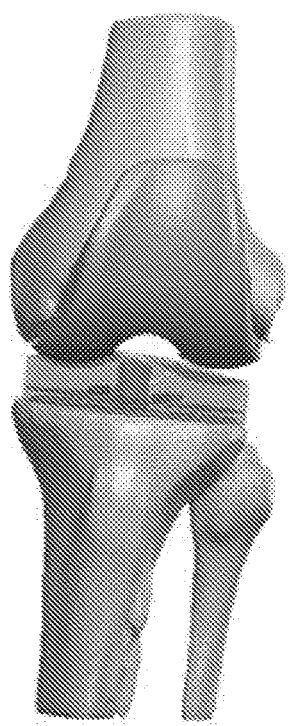
FIGS. 8a to 8f graphically illustrate predicted characteristic of the knee after surgery.
Figure 8B:
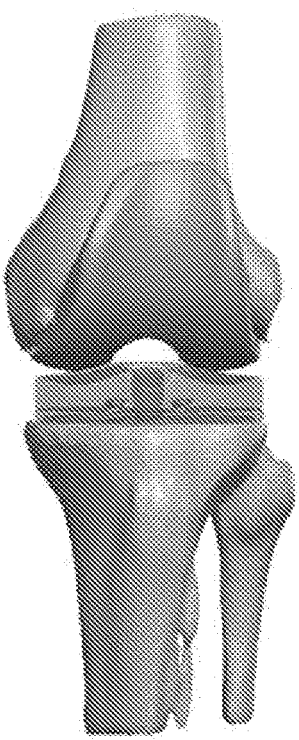
Figure 8C:
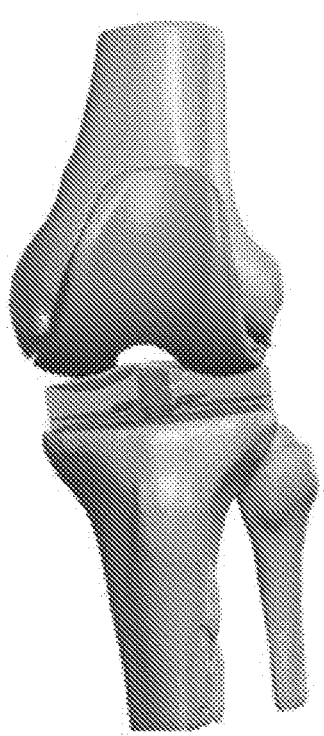
Figure 8D:
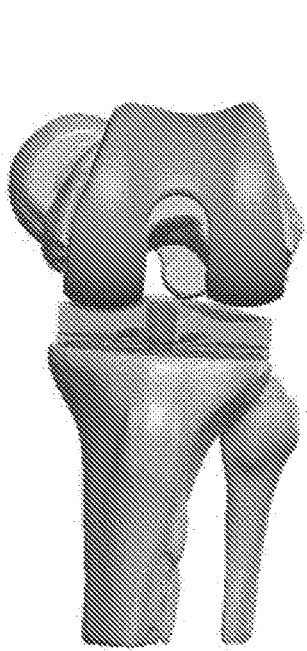
Figure 8E:
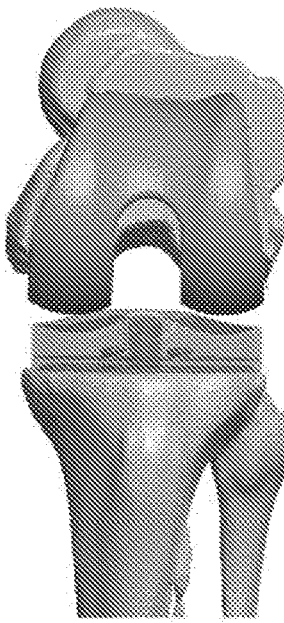
Figure 8F:
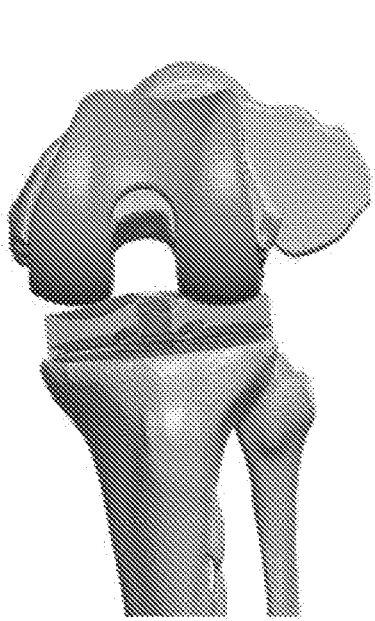

FIGS. 8a to 8f graphically illustrate the predicted characteristic of the knee after surgery in the form of rendered images of the mechanical model of the knee for the load of 6 Nm applied to the model. FIGS. 8a to 8c relate to full extension, while FIGS. 8d to 8f relate to a fully flexed knee. For example, the surgeon can clearly see that a varus torque of 6 Nm results in a predicted varus of 3 degrees at full extension (see FIG. 8a and a varus of 4 degrees at full flexion (see FIG. 8d). Further, the unloaded knee is balanced at full extension, that is has 0 degrees varus/valgus (see FIG. 8b) but has a 1 degree varus at full flexion (see FIG. 8e).

Figure 9:
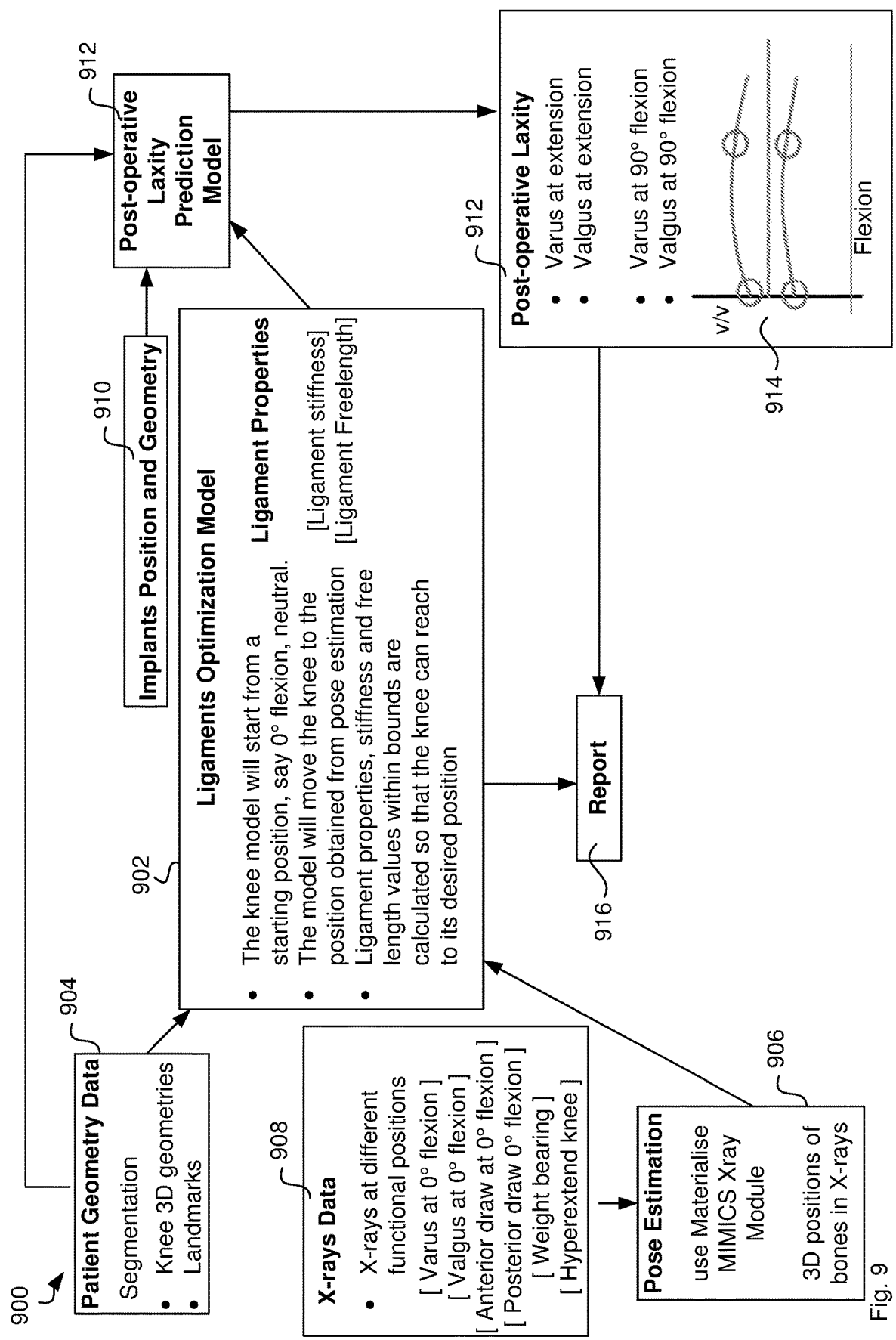
FIG. 9 illustrates another method for assisting surgery of a joint.

FIG. 9 illustrates a more detailed version of method 200 in the form of a flow chart 900. The flow chart 900 may also be implemented by corresponding software modules. The central module is a ligaments optimisation module 902 that optimises the mechanical properties of the ligaments to best fit to the observations of the movement of the bones under different mechanical loads. For these calculations ligaments optimisation module 902 receives patient geometry data from a patient geometry data module 904. The ligaments optimisation module 902 further receives measurement data, such as the three-dimensional position of bones in X-rays under different load conditions from pose estimation module 906. The pose estimation module 906, in turn, receives the X-ray data from X-ray data module 908, such as X-ray images at different functional positions including one or more of: Varus at 0° flexion, Valgus at 0° flexion, Anterior draw at 0° flexion, Posterior draw 0° flexion, Weight bearing and Hyperextend knee.

Figure 10A:
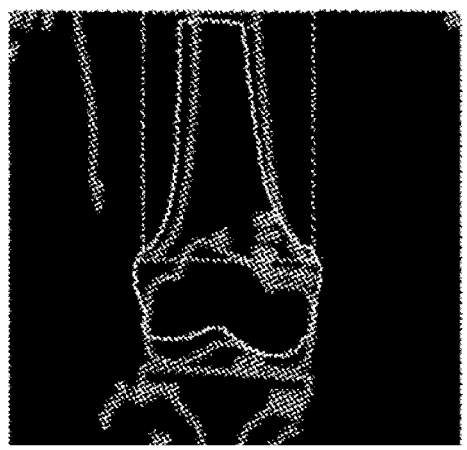
FIGS. 10a to 10d illustrate registration between X-ray image data and a mechanical model.
Figure 10B:
Figure 10C:
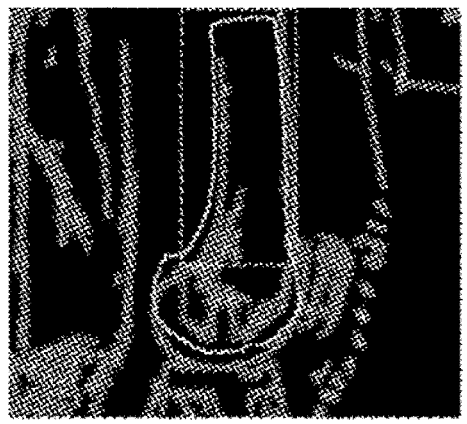
Figure 10D:
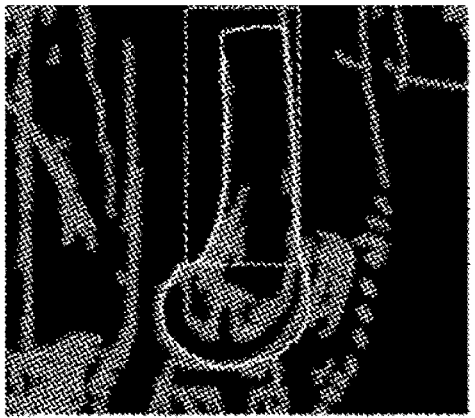

FIGS. 10a to 10d illustrate the registration step between the X-ray image data as schematically shown in FIGS. 3a and 3b and the mechanical model in FIGS. 4a and 4b. In this example, the image data is registered to a femur model. The X-ray image data in darker shading, while model outline is shown in brighter shading. This registration step may be part of the steps for determining the measurement data indicative of a movement of the bones relative to each other under multiple mechanical loads. FIGS. 10a and 10c illustrate the image data and the model before registration while FIGS. 10b and 10d illustrate the image data and the model after registration where the femur model matches the X-ray image data.

Figure 11:
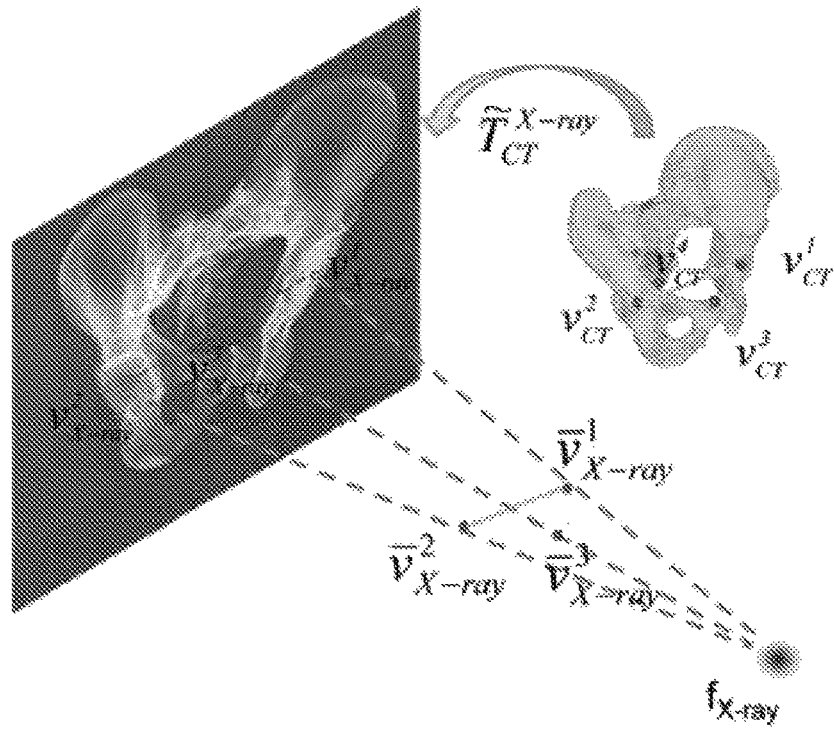
FIG. 11 illustrates an initialisation of an iterative landmark-to-ray 2D-3D registration.
Figure 12:
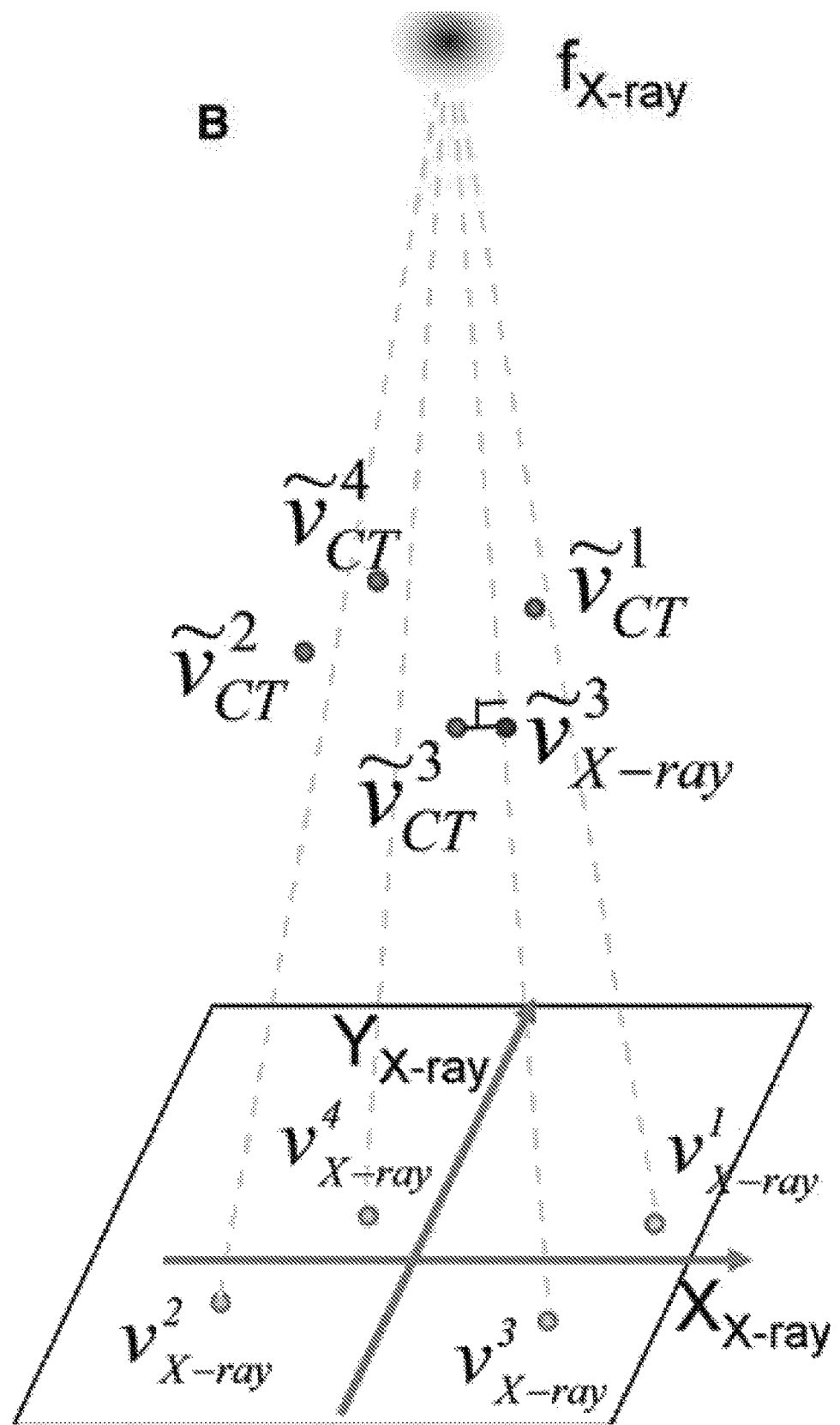
FIG. 12 illustrates finding 3D point pairs for the iterative landmark-to-ray 2D-3D registration.

FIG. 11 illustrates an initialisation of an iterative landmark-to-ray 2D-3D registration, while FIG. 12 illustrates finding 3D point pairs for the iterative landmark-to-ray 2D-3D registration.

The knee optimisation module 902 may start from a starting position, such as 0° flexion, neutral moves the knee to the position obtained from pose estimation. Processor 102 calculates ligament properties, stiffness and free length values within bounds so that the knee can reach to its desired position.

Figure 13:
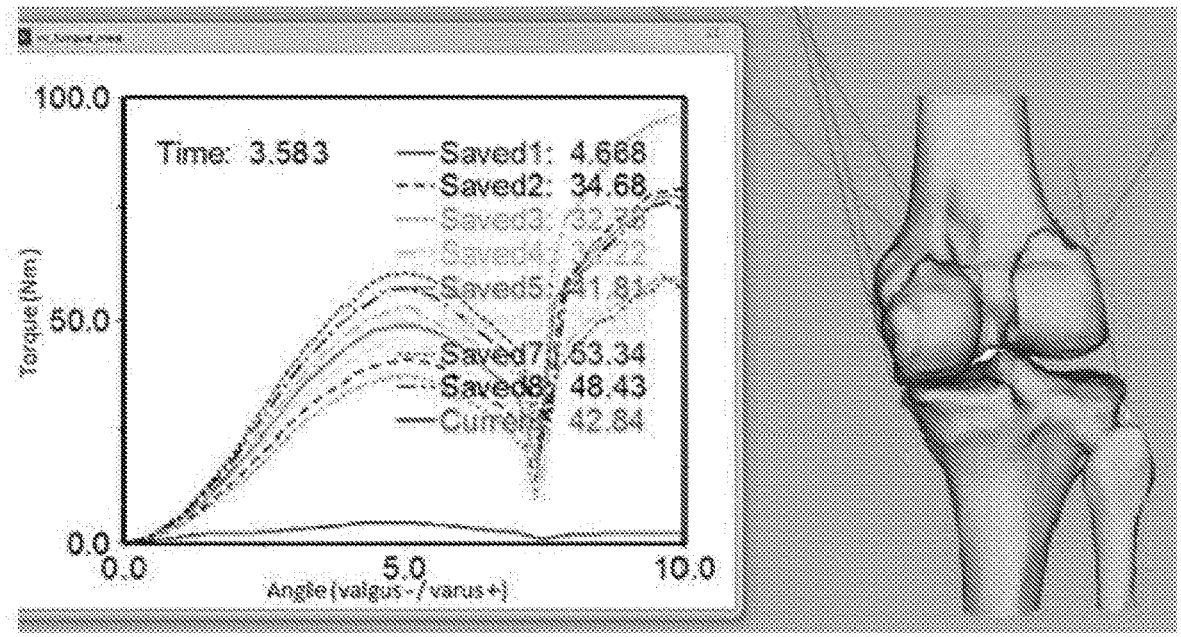
FIG. 13 illustrates an example of the optimization model.

FIG. 13 illustrates an example of the optimization model that is optimised to determine the mechanical characteristic of the ligaments. In this example, from X-ray image data the joint is at 5° varus when flexed at 20°. The ligament optimization model may iteratively change ligament stiffness and free length value to achieve equilibrium at that position. The determined ligament properties to be used later are then the values at the equilibrium.

The ligament properties together with implants position and geometry 910 and patient geometry data from patient geometry module 904 are forwarded to a post-operative laxity prediction module 912, which determines a post-operative laxity 912, such as varus at extension, valgus at extension, varus at 90° flexion and valgus at 90° flexion and a graphical representation 914 of these characteristics. These results are sent to a reporting module 916, which generates the report as described above in relation to FIGS. 5 to 8.

Figure 14:
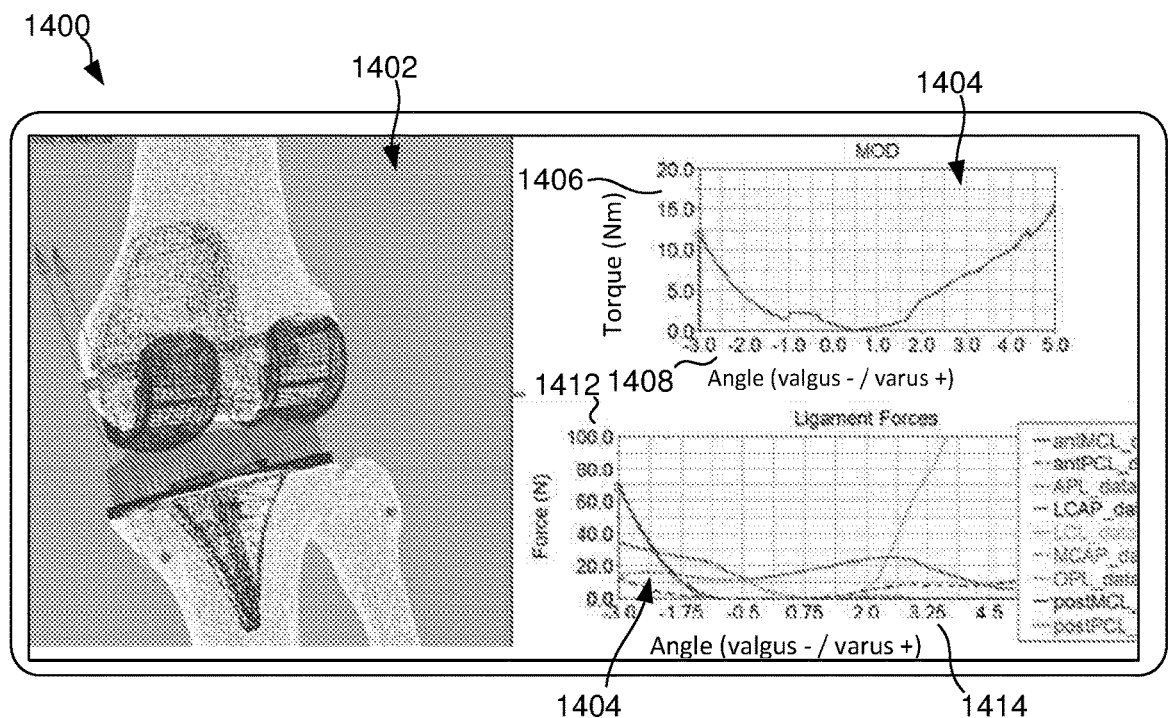
FIG. 14 illustrates a post-op laxity assessment simulation display.

FIG. 14 illustrates an example of a post-op laxity assessment simulation display 1400 comprising a three-dimensional graphical representation 1402 of the knee, which may be animated to indicate angle of flexion or angle of valgus/varus, for example. Display 1400 further comprises a first graph 1404 indicating the torque 1406 applied to the mechanical model and the resulting valgus/varus angle 1408. Display 1400 also comprises a second graph 1410 indicating the resulting simulated ligament forces 1412 of each of the multiple ligaments in the knee over the valgus/varus angle 1414, where each line in second graph 1410 represents a different ligament. Display 1400 may be provided to a surgeon during the planning phase of the surgery, such as on a screen in the consulting room of the surgeon or on a screen in theatre.

While some examples herein relate to image data that represents the movement of the bones relative to each other, it is to be understood that different measurement data may also be used, such as a direct measurement of the movement of the bones under load by measuring the positions of landmarks that are accessible through the skin or even during surgery, such as by measuring the distances from the medial or lateral condyle using a surgical calliper without the use of X-ray or other images. These methods therefore provide contact-based data since these methods are based on contacting the bones either directly or through the skin.

Further, the measurement data used to determine the mechanical properties of the ligaments may be reported computer assisted surgery data, such as kinematics between bones captured by a navigation system the as surgeon assesses the joint with various movements.

Figure 15A:
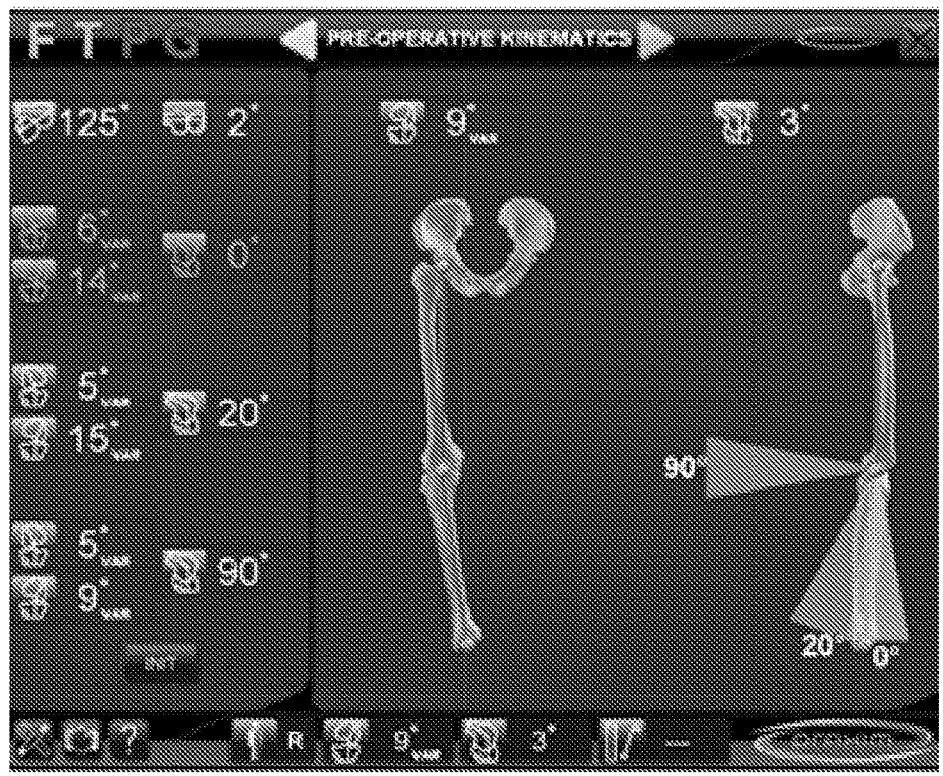
FIGS. 15a and 15b illustrate an example of a navigation system.
Figure 15B:
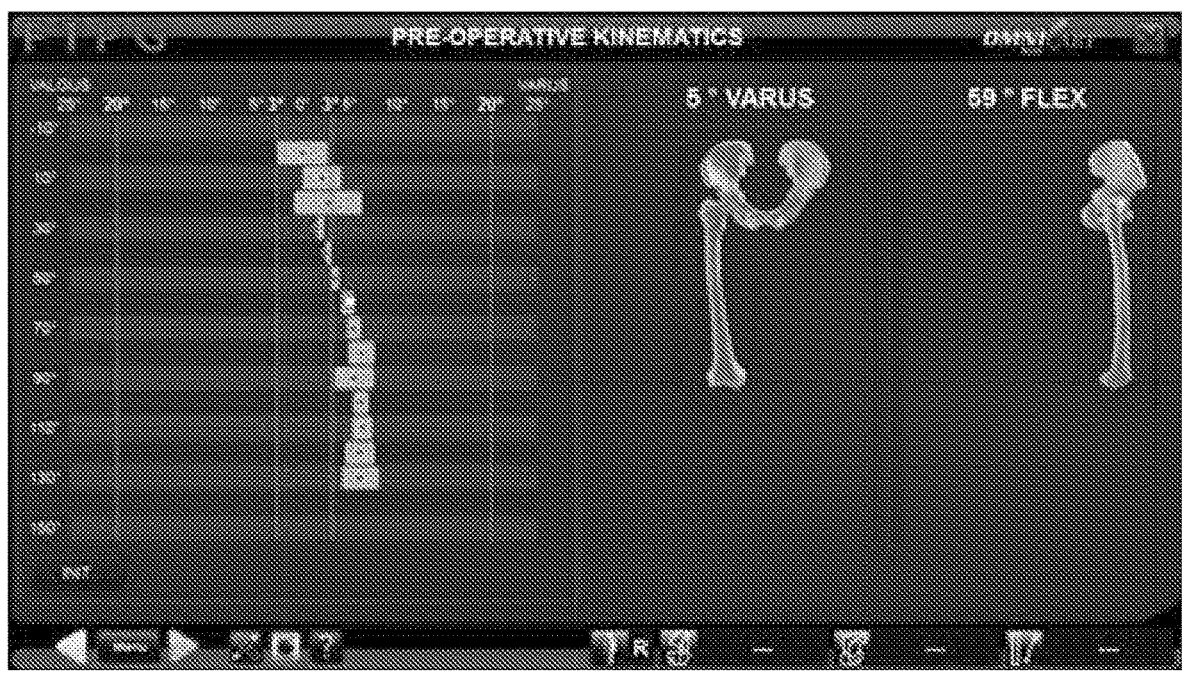

FIGS. 15a and 15b illustrate an example of a navigation system that provides different measurement data, such as varus/valgus at different flexion angles.

It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The present embodiments are, therefore, to be considered in all respects as illustrative and not restrictive.

The invention claimed is:

1. A method for assisting surgery of a joint comprising a kinematic system of two or more bones, the method comprising:
    simulating a ligament force of each of one or more ligaments associated with the joint based on pre-defined load values of multiple mechanical loads applied to the joint;
    receiving measurement data indicative of an amount of movement of the bones relative to each other as a result of the multiple mechanical loads being applied to the joint;
    evaluating a mathematical relationship between the simulated ligament force and the movement to determine a mechanical property, including a stiffness value and a length value, of each of the one or more ligaments based on the simulated ligament force and the measurement data indicative of the amount movement of the bones relative to each other;
    determining a predicted characteristic over a range of flexion of the joint after the surgery based on a planned spatial parameter of the surgery and based on the mechanical property of the one or more ligaments; and
    generating an output signal indicative of the predicted characteristic over the range of flexion of the joint to assist the surgery.

2. The method of claim 1, wherein the kinematic system comprises three or more bones.

3. The method of claim 1, wherein the spatial parameter of the surgery is a cutting angle for attaching an implant.

4. The method of claim 1, wherein determining the predicted characteristic comprises determining a predicted laxity of the joint over the range of flexion of the joint.

5. The method of claim 1, wherein generating the output signal comprises generating a display of the predicted characteristic.

6. The method of claim 1, further comprising using the output signal to optimise the spatial parameter of the surgery.

7. The method of claim 6, wherein optimising the spatial parameter of the surgery comprises adjusting a pre-defined value of the spatial parameter of the surgery.

8. The method of claim 1, further comprising determining the measurement data based on multiple first images, each of the multiple first images representing a position of the bones relative to each other under the respective mechanical load.

9. The method of claim 8, wherein each of the multiple first images is an X-ray image of the joint.

10. The method of claim 1, further comprising determining the measurement data based on contact-based data representing a position of the bones relative to each other under the respective mechanical load.

11. The method of claim 1, wherein determining the mechanical property comprises determining the mechanical property based on a spatial configuration of the joint.

12. The method of claim 11, further comprising determining the spatial configuration of the joint based on a second image of the joint.

13. The method of claim 12, wherein determining the spatial configuration of the joint comprises determining the spatial configuration of the joint based on a 3D scan of the joint.

14. The method of claim 12, wherein determining the spatial configuration of the joint comprises determining the spatial configuration of the joint based on a CT scan or MM scan or both.

15. The method of claim 1, further comprising receiving input data indicative of a desired characteristic of the joint, wherein generating an output signal comprises generating an output signal that is indicative of a correspondence between the desired characteristic and the predicted characteristic.

16. The method of claim 15, further comprising determining a modification of the one or more ligaments to adjust the predicted characteristic towards the desired characteristic based on the spatial parameter of the surgery and based on the mechanical property of the one or more ligaments,
    wherein generating an output signal comprises generating an output signal that is indicative of the modification of the one or more ligaments.

17. The method of claim 1, wherein determining the mechanical property of the one or more ligaments comprises determining the mechanical property of the one or more ligaments based on measurement data indicative of the movement of the bones relative to each other under multiple angles between the two bones.

18. The method of claim 1, wherein the joint is a knee.

19. A non-transitory computer readable medium with instructions stored thereon that, when executed by a computer, cause the computer to perform the method of claim 1.

20. A computer system for assisting surgery of a joint comprising a kinematic system of two or more bones, the computer system comprising:
    an input port to receive measurement data indicative of an amount of movement of the bones relative to each other as a result of the multiple mechanical loads applied to the joint;
    a processor to:
        simulate a ligament force of each of one or more ligaments associated with the joint based on pre-defined load values of multiple mechanical loads applied to the joint;

receive the measurement data, evaluate a mathematical relationship between the simulated ligament force and the movement to determine a mechanical property, including a stiffness value and a length value, of each of the one or more ligaments based on the simulated ligament force and the measurement data indicative of the amount movement of the bones relative to each other; and determine a predicted characteristic over a range of flexion of the joint after the surgery based on a planned spatial parameter of the surgery and based on the mechanical property of the one or more ligaments; and an output port for an output signal indicative of the predicted characteristic over the range of flexion of the joint to assist the surgery.

21. A method for assisting surgery of a joint comprising a kinematic system of two or more bones, the method comprising:

applying multiple mechanical loads with respective predefined load values to the joint;

measuring an amount of movement of the bones relative to each other as a result of the multiple mechanical loads being applied to the joint to determine measurement data;

simulating a ligament force of each of one or more ligaments associated with the joint based on the load values of the multiple mechanical loads applied to the joint;

evaluating a mathematical relationship between the simulated ligament force and the movement to determine a stiffness value of each of the one or more ligaments based on the simulated ligament force and the measurement data indicative of the amount movement of the bones relative to each other;

determining a predicted characteristic over a range of flexion of the joint after the surgery based on a planned spatial parameter of the surgery and based on the mechanical property of the one or more ligaments; and generating an output signal indicative of the predicted characteristic over the range of flexion of the joint to assist the surgery.

* * * * *